United States Patent [19]
Kawashima et al.

[11] Patent Number: 5,559,157
[45] Date of Patent: Sep. 24, 1996

[54] OPHTHALMIC COMPOSITIONS CONTAINING VITAMIN E OR ESTER THEREOF AS AN ACTIVE INGREDIENT

[75] Inventors: Yoichi Kawashima, Kyoto; Mitsuaki Kuwano, Toyonaka, both of Japan

[73] Assignee: Santen Pharmaceutical Co., LTD., Osaka, Japan

[21] Appl. No.: 64,763

[22] Filed: May 19, 1993

[30] Foreign Application Priority Data

May 26, 1992 [JP] Japan .................................. 4-133193

[51] Int. Cl.$^6$ .............................. A61F 2/14; A61K 9/54; A61K 47/36
[52] U.S. Cl. .................. 514/777; 424/427; 424/428; 514/458; 514/912; 514/913; 514/914
[58] Field of Search ..................... 424/427, 428, 424/78.04; 514/912, 913, 914, 458, 777

[56] References Cited

FOREIGN PATENT DOCUMENTS

| | | |
|---|---|---|
| 2 306684 | 5/1976 | France . |
| 60-246695 | 11/1985 | Japan . |
| 64106018 | 5/1987 | Japan . |
| 64-70413 | 3/1989 | Japan . |
| 0003689 | 5/1989 | WIPO . |
| WO89/03689 | 5/1989 | WIPO . |

OTHER PUBLICATIONS

English language translation of FR-A-2,306,684.
*Handbook of Pharmaceutical Excipients*, American Pharmaceutical Association, Washington, D.C., p.241.
Derwent Publications Ltd., London, GB; Week 8917, AN 89-125493; of JP-A-1 070 413.
Derwent Publications Ltd., London, GB; Week 8725, AN 87-174447; of JP-A-62 106 018.

*Primary Examiner*—Carlos Azpuru
*Attorney, Agent, or Firm*—Frishauf, Holtz, Goodman, Langer & Chick, P.C.

[57] ABSTRACT

This invention relates to novel aqueous ophthalmic compositions containing vitamin E or ester thereof as an active ingredient, sorbic acid or salts thereof as a preservative, and surfactant. The composition of this invention is useful for treatment of various eye diseases, especially for cataract.

22 Claims, No Drawings

OPHTHALMIC COMPOSITIONS CONTAINING VITAMIN E OR ESTER THEREOF AS AN ACTIVE INGREDIENT

BACKGROUND OF THE INVENTION

As vitamin E, a natural type of vitamin E, namely d-α-tocopherol, and synthesized vitamin E such as dl-α-tocopherol are known, and various kinds of esters thereof, for example, acetic acid ester, nicotinic acid ester, and succinic acid ester, are also well known. In this invention, such vitamin E or ester thereof is called as V-E. In the medical field, various utilities of V-E have been known, for example, a drug for defects in peripheral circulation or a suppressor for increase of lipid peroxide. Further, V-E is also known to be useful for treatment of various eye diseases. Especially, it has been reported that ophthalmics containing V-E in higher concentration could be useful for treatment of cataract (Journal of the Eye, 8, 93 (1991)).

V-E, however, is sparingly soluble in water. Therefore it is necessary to use a surfactant to formulate V-E in an aqueous ophthalmic preparation. As a prior art, a technology to dissolve or emulsify V-E in water by using surfactant such as polysorbate 80, polyoxyethylene hydrogenated castor oil or lecithin has been reported (Japanese Unexamined Patent Publication 106018/87). It is also described in prior art that rather a large amount of surfactant was needed to make an aqueous ophthalmic preparation of V-E.

To prepare multi-use type ophthalmics, which are generally used ophthalmics, a preservative is needed to prevent secondary contamination, while a surfactant may decrease the effect of the preservative.

Therefore, the decrease of the preservative effect becomes a very important problem to prepare aqueous ophthalmics of V-E which needs rather a large amount of surfactant.

Furthermore, if a preservative is formulated in a higher concentration to solve such problem, it may cause defects in eye tissues and an increase of eye irritation.

In conclusion, a study of a preservative is very important to make an aqueous ophthalmic preparation containing V-E.

DETAILED DESCRIPTION OF THE INVENTION

This invention relates to novel aqueous ophthalmic compositions containing V-E as an active ingredient, sorbic acid or salts thereof as a preservative and a surfactant.

An ophthalmic preparation of V-E is useful for treatment of various eye diseases. Especially ophthalmics containing V-E in higher concentrations is expected to be useful for treatment of cataract. V-E, however, is sparingly soluble in water, and it is necessary to use rather a large amount of surfactant to make an aqueous ophthalmic preparation of V-E. Generally used aqueous ophthalmics, a multi-use type, need a preservative to prevent secondary contamination, while a surfactant may decrease the effect of the preservative. An aqueous ophthalmic preparation of V-E needs rather a large amount of surfactant, and the decrease of the preservative effect caused by the surfactant is a very important problem. Furthermore, use of a higher concentration of a preservative should be avoided so as not to cause defects in eye tissues or an increase of eye irritation. Therefore, it is very important to provide a preservative which can be preferably used for an aqueous ophthalmic preparation of V-E.

The inventors studied to find a preferable preservative for an aqueous ophthalmic preparation of V-E.

Benzalkonium chloride or ester of p-hydroxybenzoic acid is widely used for an aqueous ophthalmic preparation as a preservative, so the inventors prepared an aqueous ophthalmic preparation using such preservative in a combination with a surfactant and examined the preservative effect. As the surfactant, polysorbate 80, a widely used surfactant, was used. The experimental result showed that the preservative effect was extremely decreased by the surfactant. It is reported that benzalkonium chloride, if the concentration is increased over 0.01%, caused corneal defects (Invest. Ophthalmol. Vis. Sci., 21, 842 (1981)).

So the inventors prepared an aqueous ophthalmic preparation of V-E formulating benzalkonium chloride in a concentration of 0.01%, the upper limit which does not cause corneal defects, and examined the preservative effect. However, the preservative effect was not satisfactory for the ophthalmic preparation. Ester of p-hydroxybenzoic acid has properties similar to benzalkonium chloride. That is to say, the increased formulating amount causes defects in eye tissues or increase of eye irritation.

Thus the inventors made a study to find a preferable preservative which has a satisfactory presevative effect, does not cause defects in eye tissues and causes little eye irritation, and to prepare an aqueous ophthalmic preparation using the preferable preservative. The inventors presumed that the decrease of the preservative effect depended on taking the preservative in the surfactant, and investigated a preservative which could hardly be taken in a surfactant. As the result of the precise study, the inventors found that sorbic acid or salts thereof (hereinafter called merely sorbic acid if not otherwise specified) shows a satisfactory preservative effect in an concentration of 0.1% or over even if rather a large amount of surfactant is used. Further, the inventors examined possibility of causing defects in eye tissues or eye irritation, which is another important problem for an ophthalmic preparation, and found that the aqueous ophthalmic preparation using sorbic acid as a preservative hardly caused defects in eye tissues and eye irritation. The test was made using rabbits' eyes. In conclusion, the inventors succeeded in preparing an aqueous ophthalmic preparation of V-E, which showed satisfactory preservative effect and hardly caused defects in eye tissues and eye irritation, by formulating sorbic acid as a preservative.

The characteristic of this invention is an aqueous ophthalmic composition which contains V-E as an active ingredient, sorbic acid or salts thereof as a preservative, and a surfactant.

Definition of various terms in this invention are explained as follows. An aqueous ophthalmic preparation means a clear solution in which V-E is dissolved in an aqueous vehicle clearly, or an emulsion in which V-E is emulsified in an aqueous vehicle.

V-E means natural or synthesized vitamin E such as d-α-tocopherol or dl-α-tocopherol, or an ester thereof such as acetic acid ester, nicotinic acid ester or succinic acid ester.

The salt of sorbic acid is exemplified by sodium salt or potassium salt.

The concentration of V-E in this invention is preferably 0.1–10%, more preferably 0.5–5%. Examples of surfactants are polysorbate 80, polyoxyethylene hydrogenated castor oil, lecithin, fatty acid ester of sucrose, polyoxyethylene alkyl ether, polyoxy stearate, and polyoxyethylene polyoxypropylene glycol. A preferable surfactant is "POLYSORBATE 80" (a mixture of polyoxyethylene esters of mixed partial oleic esters of sorbitol anhydrides) or polyoxyethylene hydrogenated castor oil. The amount of the surfactant is 0.2–30 times the amount of V-E, preferably 0.3–10 times.

The concentration of sorbic acid depends on the amount of V-E or the surfactant, but usually 0.1–2.0%, preferably 0.1–1.0%.

If edetic acid or salts thereof is formulated in the preparation of this invention, the preservative effect of the sorbic acid can be increased. The amount of edetic acid or salts thereof, which can be formulated according to necessity, is 0.001–0.1%, preferably 0.003–0.05%.

According to the invention, a preferable aqueous ophthalmic composition contains 0.1–10% of acetic acid ester of d-α-tocopherol, 0.25–2.5% of POLYSORBATE 80 or polyoxyethylene hydrogenated castor oil, and 0.1–1.0% of sorbic acid or salts thereof.

The preparation of this invention can be preferably used for an aqueous ophthalmic preparation having a higher concentration of V-E, for example, an ophthalmic for cataract.

The ophthalmic preparation of this invention can be prepared by mixing V-E with a surfactant followed by addition of sterile purified water containing sorbic acid, and if necessary, isotonic agent such as sodium chloride or glycerol, a buffering agent such as sodium phosphate, a pH adjusting agent such as dilute hydrochloric acid or sodium hydroxide, sodium edetate which plays a role of increasing the preservative effect, etc. can be added.

The generally used range of pH can be used for this preparation, but a preferable range is 4–8.

Examples are shown below.

EXAMPLE 1

| Formulation 1 (100 ml) | |
|---|---|
| d-α-tocopherol acetate | 1.0 g |
| potassium sorbate | 0.1 g |
| polysorbate 80 | 0.5 g |
| sodium chloride | 0.9 g |
| sodium edetate | 0.01 g |
| sodium hydroxide | q.s. |
| diluted hydrochloric acid | q.s. |

Preparation Method:

To a mixture of acetic acid ester of d-α-tocopherol and POLYSORBATE 80, sterile purified water dissolving potassium sorbate, sodium chloride and sodium edetate was added while stirring, followed by addition of sodium hydroxide and diluted hydrochloric acid to adjust pH to 6.5. White emulsion was thus obtained.

The following ophthalmics, formulations 2 to 6, can be prepared by a similar procedure.

| Formulation 2 (100 ml) | |
|---|---|
| d-α-tocopherol acetate | 1.0 g |
| potassium sorbate | 0.2 g |
| POLYSORBATE 80 | 0.5 g |
| sodium chloride | 0.81 g |
| sodium edetate | 0.01 g |
| sodium hydroxide | q.s. |
| diluted hydrochloric acid | q.s. |

| Formulation 3 (100 ml) | |
|---|---|
| d-α-tocopherol acetate | 0.5 g |
| potassium sorbate | 0.2 g |
| POLYSORBATE 80 | 0.25 g |
| sodium chloride | 0.81 g |
| sodium edetate | 0.01 g |
| sodium hydroxide | q.s. |
| diluted hydrochloric acid | q.s. |

| Formulation 4 (100 ml) | |
|---|---|
| d-α-tocopherol acetate | 0.1 g |
| potassium sorbate | 0.1 g |
| POLYSORBATE 80 | 0.2 g |
| sodium chloride | 0.81 g |
| sodium edetate | 0.003 g |
| sodium hydroxide | q.s. |
| diluted hydrochloric acid | q.s. |

| Formulation 5 (100 ml) | |
|---|---|
| d-α-tocopherol | 5.0 g |
| potassium sorbate | 1.0 g |
| polyoxyethylene hydrogenated castor oil | 2.5 g |
| sodium chloride | 0.8 g |
| sodium edetate | 0.05 g |
| sodium hydroxide | q.s. |
| diluted hydrochloric acid | q.s. |

| Formulation 6 (100 ml) | |
|---|---|
| d-α-tocopherol acetate | 1.0 g |
| sodium sorbate | 0.2 g |
| POLYSORBATE 80 | 0.3 g |
| sodium chloride | 0.8 g |
| sodium edetate | 0.01 g |
| sodium hydroxide | q.s. |
| diluted hydrochloric acid | q.s. |

EXAMPLE 2

| Formulation 7 (100 ml) | |
|---|---|
| d-α-tocopherol acetate | 0.5 g |
| potassium sorbate | 0.2 g |
| POLYSORBATE 80 | 5.0 g |
| sodium chloride | 0.81 g |
| sodium edetate | 0.01 g |
| sodium hydroxide | q.s. |
| diluted hydrochloric acid | q.s. |

Preparation Method:

To a mixture of acetic acid ester of d-α-tocopherol and POLYSORBATE 80, sterile purified water dissolving potassium sorbate, sodium chloride and sodium edetate was added while stirring, followed by addition of sodium hydroxide and diluted hydrochloric acid to adjust pH to 6.5. A clear solution was thus obtained.

The following ophthalmics, formulations 8, can be prepared by a similar procedure.

| Formulation 8 (100 ml) | |
|---|---|
| d-α-tocopherol nicotinate | 0.2 g |
| potassium sorbate | 0.5 g |
| polyoxyethylene hydrogenated castor oil | 2.0 g |
| sodium chloride | 0.8 g |
| sodium edetate | 0.01 g |
| sodium hydroxide | q.s. |
| diluted hydrochloric acid | q.s. |

Examination of preservative effect

To examine the preservative effect of sorbic acid, a preservative test was performed on the ophthalmic preparations of formulations 1 and 2 according to US pharmacopoeia.

For comparison, a preservative test was also performed on the following Comparative Formulations 1, 2 and 3 which contain benzalkonium chloride or ester of p-hydroxybenzoic acid.

| Comparative Formulation 1 (100 ml) | |
|---|---|
| d-α-tocopherol acetate | 1.0 g |
| benzalkonium chloride | 0.005 g |
| POLYSORBATE 80 | 0.5 g |
| sodium chloride | 0.9 g |
| sodium edetate | 0.01 g |
| sodium hydroxide | q.s. |
| diluted hydrochloric acid | q.s. |
| Comparative Formulation 2 (100 ml) | |
| d-α-tocopherol acetate | 1.0 g |
| benzalkonium chloride | 0.01 g |
| POLYSORBATE 80 | 0.5 g |
| sodium chloride | 0.9 g |
| sodium edetate | 0.01 g |
| sodium hydroxide | q.s. |
| diluted hydrochloric acid | q.s. |
| Comparative Formulation 3 (100 ml) | |
| d-α-tocopherol acetate | 1.0 g |
| methyl paraben | 0.052 g |
| propyl paraben | 0.028 g |
| POLYSORBATE 80 | 0.5 g |
| sodium chloride | 0.9 g |
| sodium edetate | 0.01 g |
| sodium hydroxide | q.s. |
| diluted hydrochloric acid | q.s. |

Test Result:

The decrease of bacteria, which was incubated in the medium ($3.86 \times 10^5$/ml), was calculated after two weeks and the result was shown in Table 1 by the percentage of the decrease of bacteria.

TABLE 1

| bacteria | Formulation 1 | Formulation 2 | Comparative Formulation 1 | Comparative Formulation 2 | Comparative Formulation 3 |
|---|---|---|---|---|---|
| Escherichia coli | 99% | 100% | 100% | 100% | 88% |
| Pseudomonus aeruginosa | 99% | 99% | increased | increased | increased |
| Staphylococcus aureus | >99.9% | >99.9% | >99.9% | >99.9% | 95% |
| Aspergillus niger | 99% | >99% | 55% | 96% | 9% |

As shown in Table 1, *Pseudomonus aeruginosa* was decreased by 99% in the formulations 1 and 2 of this invention. On the contrary, in the comparative formulations *Pseudomonus aeruginosa* was increased. Furthermore, formulation 1 and 2 containing sorbic acid showed excellent suppressive effect on *Aspergillus niger*. The results clearly show the preservative effect of sorbic acid.

Test for Safety to Eye

Experimental method:

The ophthalmic preparation of the formulation 2, an example of the preparation of this invention, was instilled to Japanese white male rabbits (5 rabbits a group) for 4 weeks, 5 times a day. After 4 weeks, visual observation was made on anterior segment.

Result:

Disorders such as redness and edema were not observed on cornea, conjunctiva or iris. Eye irritation was also examined according to improved Draze method (Gendai no Rinsho, 4(7), 277 (1970)), and eye irritation was hardly found on the ophthalmic preparation of this invention.

What we claim is:

1. An aqueous ophthalmic composition for those in need thereof which comprises (a) 0.5 to 5 weight % of an active ingredient selected from the group consisting of vitamin E and an ester thereof selected from the group consisting of an acetic acid ester, a nicotinic acid ester and a succinic acid ester, (b) 0.1 to 2.0 weight % of a preservative selected from the group consisting of sorbic acid and a salt thereof selected from the group consisting of a sodium salt and a potassium salt, and (c) a surfactant selected from the group consisting of (i) a mixture of polyoxyethylene esters of mixed partial oleic esters of sorbitol anhydrides and (ii) polyoxyethylene hydrogenated castor oil, said surfactant being in an amount of 0.2 to 30 times the amount of said active ingredient selected from the group consisting of vitamin E and an ester thereof.

2. The aqueous ophthalmic composition as in claim 1, wherein the preservative selected from the group consisting of sorbic acid and said salt thereof is in an amount of 0.1–1.0 weight %.

3. The aqueous ophthalmic composition as in claim 1, which is in the form of an emulsion.

4. The aqueous ophthalmic composition as in claim 1, which is in the form of a clear solution.

5. An aqueous ophthalmic composition for those in need thereof which comprises (a) 0.5 to 5 weight % of an active ingredient selected from the group consisting of vitamin E and an ester thereof selected from the group consisting of acetic acid ester, a nicotinic acid ester and a succinic acid ester, (b) 0.1 to 2.0 weight % of a preservative selected from the group consisting of sorbic acid and a salt thereof selected from the group consisting of a sodium salt and a potassium salt, (c) 0.001 to 0.1 weight % edetic acid or a sodium salt thereof, and (d) a surfactant selected from the group consisting of (i) a mixture of polyoxyethylene esters of mixed partial oleic esters of sorbitol anhydrides and (ii) polyoxyethylene hydrogenated castor oil, said surfactant being in an amount of 0.2 to 30 times the amount of said active ingredient selected from the group consisting of vitamin E and an ester thereof.

6. An aqueous ophthalmic composition comprising (a) 0.1 to 10 weight % of acetic acid ester of d-α-tocopherol, (b) 0.25–2.5 weight % of a mixture of polyoxyethylene esters of mixed partial oleic esters of sorbitol anhydrides or polyoxyethylene hydrogenated castor oil, and (c) 0.1–1.0 weight % of a preservative selected from the group consisting of sorbic acid and a salt thereof selected from the group consisting of a sodium salt and a potassium salt.

7. The aqueous ophthalmic composition as in claim 2, which is in the form of an emulsion.

8. The aqueous ophthalmic composition as in claim 2, which is in the form of a clear solution.

9. The aqueous ophthalmic composition as in claim 1, wherein the amount of the surfactant is 0.3 to 10 times the amount of the active ingredient selected from the group consisting of vitamin E and an ester thereof; and the preservative selected from the group consisting of sorbic acid and said salt thereof being in a concentration of 0.1 to 1.0 weight %.

10. The aqueous ophthalmic composition as in claim 5, wherein the amount of the surfactant is 0.3 to 10 times the amount of the active ingredient selected from the group consisting of vitamin E and an ester thereof; the preservative selected from the group consisting of sorbic acid and said salt thereof being in a concentration of 0.1 to 1.0 weight %; and the amount of the edetic acid or said sodium salt thereof being 0.001 to 0.1 weight %.

11. The aqueous ophthalmic composition as in claim 10, wherein the amount of the edetic acid or said sodium thereof being 0.003 to 0.05% weight.

12. An aqueous ophthalmic composition comprising (a) 0.5 to 5 weight % of an acetic acid ester of d-α-tocopherol, (b) 0.25 to 2.5 weight % of a mixture of polyoxyethylene esters of mixed partial oleic esters of sorbitol anhydrides or 0.25 to 2.5 weight % of polyoxyethylene hydrogen castor oil and (c) 0.1 to 1.0 weight % of a preservative selected from the group consisting of sorbic acid and a salt thereof selected from the group consisting of a sodium salt and a potassium salt.

13. An aqueous ophthalmic composition comprising (a) 1.0 weight % of an acetic acid ester of d-α-tocopherol, (b) 0.5 weight % of a mixture of polyoxyethylene esters of mixed partial oleic esters of sorbitol anhydrides and (c) 0.2 weight % of potassium sorbate.

14. The composition as in claim 5, wherein the sorbic acid or said salt thereof is in an amount of 0.1–1.0 weight %.

15. The aqueous ophthalmic composition as in claim 5, which is in the form of an emulsion.

16. The aqueous ophthalmic composition as in claim 5, which is in the form of a clear solution.

17. The aqueous ophthalmic composition as in claim 14, which is in the form of an emulsion.

18. The aqueous ophthalmic composition as in claim 14, which is in the form of a clear solution.

19. An aqueous ophthalmic composition comprising (a) 0.1 to 10 weight % of an acetic acid ester of d-α-tocopherol, (b) 0.1 to 1.0 weight % of a preservative selected from the group consisting of sorbic acid and a salt thereof selected from the group consisting of a sodium salt and a potassium salt, (c) 0.25 to 2.5 weight % of a mixture of polyoxyethylene esters of mixed partial oleic esters of sorbitol anhydrides or 0.25 to 2.5 weight % of a polyoxyethylene hydrogen castor oil and (d) 0.001 to 0.1 weight % of an edetic acid or a sodium salt thereof.

20. An aqueous ophthalmic composition comprising (a) 0.5 to 5 weight % of an acetic acid ester of d-α-tocopherol, (b) 0.1 to 1.0 weight % of a preservative selected from the group consisting of sorbic acid and a salt thereof selected from the group consisting of a sodium salt and a potassium salt, (c) 0.25 to 2.5 weight % of a mixture of polyoxyethylene esters of mixed partial oleic esters of sorbitol anhydrides or 0.25 to 2.5 weight % of a polyoxyethylene hydrogen castor oil and (d) 0.003 to 0.05 weight % of an edetic acid or a sodium salt thereof.

21. An aqueous ophthalmic composition comprising (a) 1.0 weight % of an acetic acid ester of d-α-tocopherol, (b) 0.2 weight % of a preservative selected from the group consisting of sorbic acid and a salt thereof selected from the group consisting of a sodium salt and a potassium salt, (c) 0.5 weight % of a mixture of polyoxyethylene esters of mixed partial oleic esters of sorbitol anhydrides and (d) 0.01 weight % of an edetic acid or a sodium salt thereof.

22. The aqueous ophthalmic composition as in claim 1, wherein the surfactant is 0.25 to 2.5 weight % of the mixture of polyoxyethylene ester of mixed partial oleic esters of sorbitol anhydrides; and said preservative is in an amount of 0.2 weight %.

* * * * *